(12) United States Patent
Goodbread et al.

(10) Patent No.: US 10,184,881 B2
(45) Date of Patent: Jan. 22, 2019

(54) CORROSION TIME PROFILE MEASUREMENT DEVICE

(71) Applicant: Rheonics GmbH, Winterthur (CH)

(72) Inventors: Joseph H. Goodbread, Winterthur (CH); Sunil Kumar, Winterthur (CH); Klaus Haeusler, Zurich (CH)

(73) Assignee: RHEONICS GMBH, Winterthur (CH)

( * ) Notice: Subject to any disclaimer, the term of this patent is extended or adjusted under 35 U.S.C. 154(b) by 0 days.

(21) Appl. No.: 15/567,017

(22) PCT Filed: Apr. 18, 2016

(86) PCT No.: PCT/US2016/028156
§ 371 (c)(1),
(2) Date: Oct. 16, 2017

(87) PCT Pub. No.: WO2016/168842
PCT Pub. Date: Oct. 20, 2016

(65) Prior Publication Data
US 2018/0120217 A1    May 3, 2018

Related U.S. Application Data

(60) Provisional application No. 62/149,392, filed on Apr. 17, 2015.

(51) Int. Cl.
*G01N 17/04*    (2006.01)
*G01N 29/265*    (2006.01)
*G01N 29/02*    (2006.01)
*G01N 29/036*    (2006.01)

(52) U.S. Cl.
CPC ............ *G01N 17/04* (2013.01); *G01N 29/022* (2013.01); *G01N 29/036* (2013.01); *G01N 29/265* (2013.01); *G01N 2291/0258* (2013.01); *G01N 2291/02818* (2013.01); *G01N 2291/0426* (2013.01); *G01N 2291/0427* (2013.01)

(58) Field of Classification Search
CPC ............................. G01N 17/04; G01N 19/022
See application file for complete search history.

(56) References Cited

U.S. PATENT DOCUMENTS

| | | | |
|---|---|---|---|
| 3,253,219 A * | 5/1966 | Littler | G01N 17/04 29/25.35 |
| 2002/0105346 A1 | 8/2002 | Banke | |
| 2002/0178787 A1 | 12/2002 | Matsiev et al. | |

(Continued)

*Primary Examiner* — John Chapman, Jr.
(74) *Attorney, Agent, or Firm* — Timothy E. Siegal Patent Law, PLLC; Timothy E. Siegal

(57) ABSTRACT

A method of measuring the amount of corrosion of a target material caused exposure to a fluid, over a period of time, utilizing a corrosion measuring device, including a resonator having a first surface area made of a material having a corrosion profile like that of the target material and having a second surface area made of material having a corrosion profile unlike that of the target material; and a transducer assembly, positioned to drive the resonator and sense resultant resonator motion, thereby producing a sense signal. In the method, the resonator is exposed to the target fluid over the period of time and the sense signal is analyzed over the period of time to determine changes in how the resonator responds to being driven by the transducer assembly, over time.

26 Claims, 17 Drawing Sheets

(56) References Cited

U.S. PATENT DOCUMENTS

| | | |
|---|---|---|
| 2002/0178805 A1 | 12/2002 | Difoggo |
| 2007/0159187 A1 | 7/2007 | Chen et al. |
| 2007/0199379 A1* | 8/2007 | Wolf ................. G01N 17/04 73/590 |
| 2008/0215245 A1 | 9/2008 | Reittenger |
| 2013/0167620 A1* | 7/2013 | Haeusler ............ G01N 11/16 73/54.41 |

* cited by examiner

CORROSION TIME PROFILE MEASUREMENT DEVICE

BACKGROUND

Field of the Invention

The field of the invention is corrosion monitoring devices and methods.

Background Art

Corrosion of fluid transport and processing equipment is a serious problem that brings high costs to infrastructure maintenance. Methods are known for monitoring and preventing corrosion, but as will be shown, each carries with it certain disadvantages or limitations.

A commonly used prior art device consists of a rectangular or disk-shaped coupon of the material whose corrosion is to be monitored, affixed to mounting means that enable the coupon to be inserted into a pipeline, tank, or any enclosure whose corrosion is to be monitored. The weight of the coupon is measured prior to installation. After a period of time, the coupon is extracted from the fluid and again weighed, the weight loss being used to estimate the corrosion rate of the coupon. Since it would be commercially advantageous to be able to substitute a real-time corrosion measurement for the coupon method, it would be advantageous to embody the specified method in the form of a probe-shaped system. The probe-shaped system could then easily be used to retro-fit existing corrosion monitoring systems based on weight loss of coupons. Such systems could transmit their operational parameters, namely temperature of the fluid, and resonant frequency and damping of the resonator, to a telemetry station removed from the site of the measurement, obviating the need for regular on-site operator intervention.

SUMMARY

In a first separate aspect, the present invention may take the form of a method of measuring the amount of corrosion of a target material caused exposure to a fluid, over a period of time, utilizing a corrosion measuring device, including a resonator having a first surface area made of a material having a corrosion profile like that of the target material and having a second surface area made of material having a corrosion profile unlike that of the target material; and a transducer assembly, positioned to drive the resonator and sense resultant resonator motion, thereby producing a sense signal. In the method, the resonator is exposed to the target fluid over the period of time and the sense signal is analyzed over the period of time to determine changes in how the resonator responds to being driven by the transducer assembly, over time.

In a second separate aspect, the present invention may take the form of a corrosion measuring device for measuring the tendency of a target fluid to corrode a target material. The device includes a resonator having a first surface area made of a material having a corrosion profile like that of the target material and having a second surface area made of material having a corrosion profile unlike that of the target material. Also, a transducer assembly is positioned to drive the resonator and sense resultant resonator motion, thereby producing a sense signal. Finally, a data processing assembly is adapted to receive the sense signal and analyze it to determine a change in resonator response to being driven by the transducer assembly.

BRIEF DESCRIPTION OF THE DRAWINGS

Exemplary embodiments are illustrated in referenced drawings. It is intended that the embodiments and figures disclosed herein are to be considered illustrative rather than restrictive.

PREFERRED MODES OF CARRYING OUT THE INVENTION

When used in this application the term "corrosion profile" means the tendency of a material to be corroded by each of an array of different corrosive fluids. Materials having like corrosion profiles are susceptible to corrosion by the same corrosive fluids, whereas materials having unlike corrosion profiles are susceptible to differing corrosive fluids. A second material, having a corrosion profile unlike that of a first material, may be generally less susceptible to corrosion.

Preferred embodiments of the present invention may provide a corrosion monitoring method that meets the needs of inexpensive, long term, sensitive, inline corrosion monitoring that enables real-time telemetry of corrosion rates at multiple sites in an installation. Real-time monitoring enables feedback controlled dosing of anticorrosion chemicals at a suitable rate to ensure minimal corrosion rates without the expense and environmental burden of overdosing or a safety breach.

In broad overview, a symmetric resonator, for example in the form of a torsional tuning fork, is fitted with two tines of dissimilar materials, one of which is known to be resistant to corrosion in a given fluid, and the second of a material whose corrosion in the fluid is to be measured. The two tines are so constituted as to individually have the same resonant frequency. They are mounted on a common base, the base being compliantly connected to a second inertial base having a much larger moment of inertia than the entire tuning fork assembly about the connecting point between it and the tuning fork.

When the two tines are in their as-manufactured state, the tuning fork is balanced; that is, when it is vibrating in its second torsional (symmetric) mode, in which the two tines rotate in opposite directions so that the mode possesses mirror symmetry about a plane perpendicular to the axes of the two tines, the reaction torque on the common base is a minimum. Any change in the difference of the masses of the two tines will result in an increase of the imbalance between the two tines, further resulting in an increase of the reaction torque on the common base.

If the connection between the common base and the inertial base is made compliant, then the reaction torque due to the unbalanced torsional resonance will produce a periodic torsional oscillation of the common base, which can be measured by one of many known means, as, for example, an electromagnetic angular velocity sensor.

Figure 1:
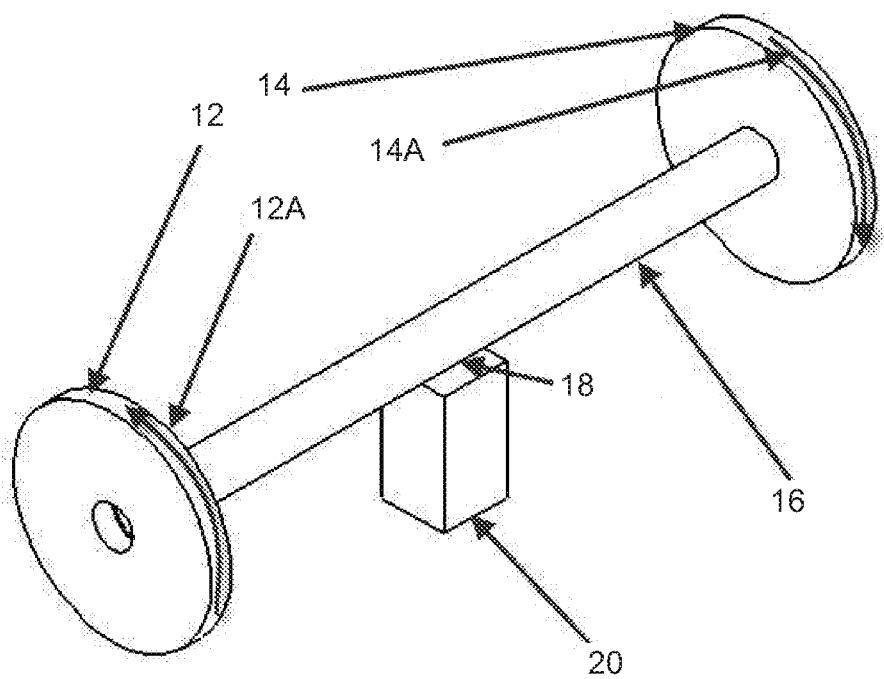
FIG. 1 depicts a simplified symmetrical torsional mass-spring system.
Figure 2:
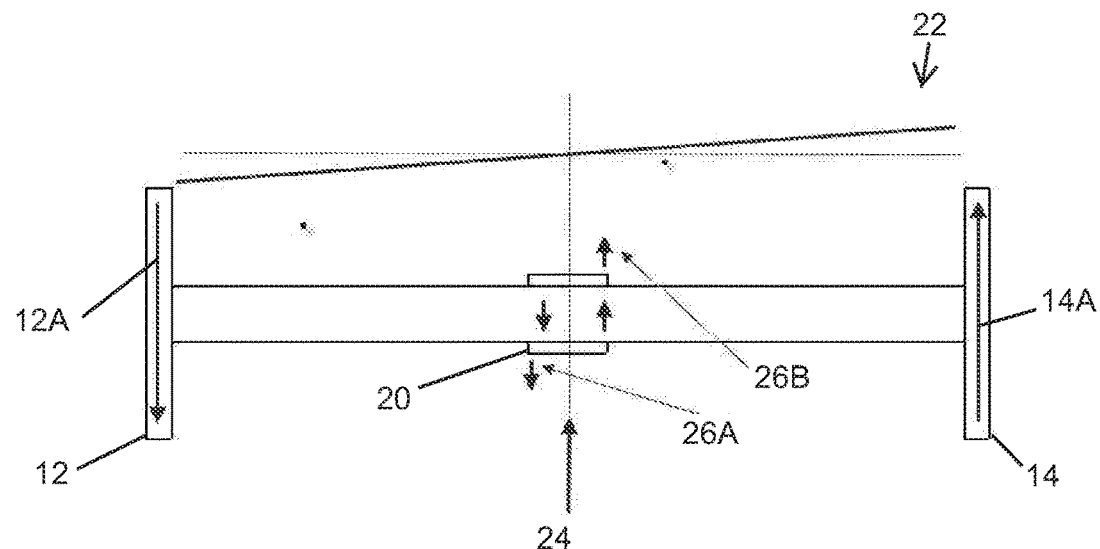
FIG. 2 illustrates the motion of the system components of FIG. 1.

In one preferred embodiment, a simplified symmetrical torsional mass-spring system 10 consists of two inertial masses 12 and 14 having the same moment of inertia, as shown in FIG. 1. The inertial masses rotate in opposite directions, indicated by arrows 12A and 14A, when driven at a first antisymmetric modal frequency. The torsion spring 16, uniform along its length, is attached via a glue bond 18 to a compliant nodal support 20 whose effective shear stiffness is much smaller than the shear rigidity of the torsion spring 16. Because it is glued to the spring 16, and is much more compliant than the spring 16, the compliant nodal support 20 will be sheared freely by the shearing of the torsion spring 16. FIG. 2 illustrates the motion of the components of the system 10, and the symmetrical angular displacement 22 along the length of the spring 16. Because the system 10 is perfectly symmetrical with respect to its median plane or node 24, the support 20 experiences pure shearing, indicated by arrows 26A and 26B, with no translation.

Figure 3:
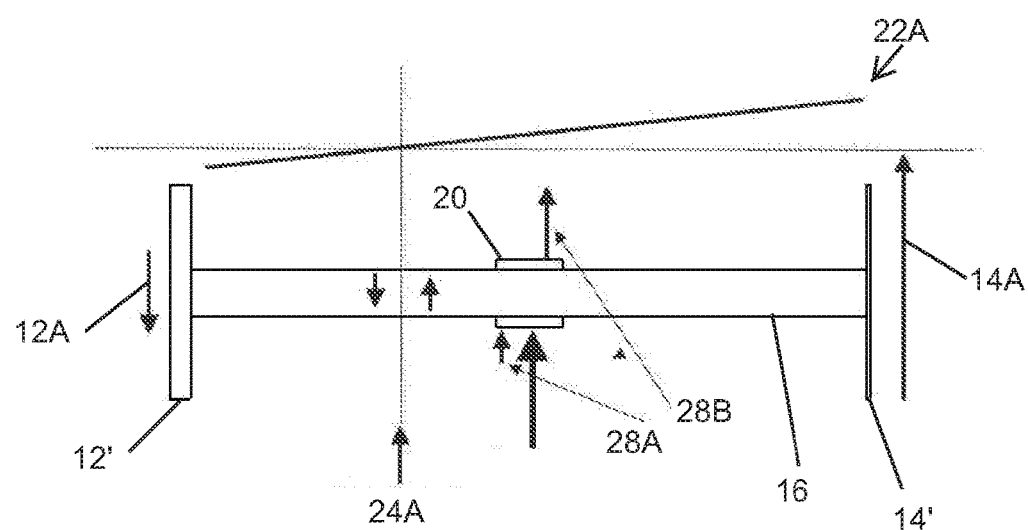
FIG. 3 illustrates the motion of the system components of FIG. 1 when the inertia of one of the end masses is reduced substantially.

Referring to FIG. 3, the inertia of one of the end masses 14' is reduced substantially as shown in FIG. 3, with the arrows 12A and 14A showing the directions in which the masses rotate. The larger of the two masses 12' becomes, in the limit, a node, vibrating with substantially less angular amplitude than the end with the smaller mass 14'. One consequence is that the resonant frequency of the system is increased, resulting in shifted node 24A positioned toward the more massive end 12'. A second consequence is that the support 20 no longer experiences pure shearing, but now shows a translational component, with arrows 28A and 28B showing the displacement of support 20. The magnitude of the translation of the support 20 is therefore a measure of the imbalance of the resonator, providing that the resonator is driven in such a manner as to oscillate at its first antisymmetric modal frequency. To accomplish this, it is possible to use some sort of tracking excitation scheme, such as that described in U.S. Pat. No. 8,291,750 that ensures that the excitation frequency keeps the system at the appropriate eigenfrequency. Any scheme that keeps the system at the appropriate resonant frequency in the face of temperature and pressure changes, as well as changes in the mass distribution of the resonator, will suffice. Furthermore, the translational movement of the support will be at the excitation frequency, so that synchronous detection schemes can be used to measure very small changes in the translational motion of the support.

In a third preferred embodiment (not shown, but with numbers assigned to elements in similar manner to the reference numbers of FIGS. 1-4), the compliant support 20 is in the form of a leaf spring 30, attached to the torsion spring 16 at its original nodal point 24. The leaf spring 30 is so dimensioned as to have much higher torsional compliance than the torsion spring 16 connecting the two end masses 12 and 14. In addition, it is also highly compliant in bending, so that it is free to both twist and translate as the nodal point of the torsional resonator 24 moves in response to changes of its end masses 12 and 14. The excitation and sensing means 32 for the torsional resonance of the system 10 are not shown in any detail, but the transducers can be electromagnetic, piezoelectric, or any other device that is conducive to exciting and measuring the desired vibrational mode.

A further requirement is that the two end masses 12 and 14 have initially the same moment of inertia. If the reference material has a different density from that of the material under test, the reference mass 12 must be scaled dimensionally so as to have the same moment of inertia as the test mass 14. If the two masses 12 and 14 are of the same initial diameter, the thickness of each mass is required to be inversely proportional to its density. Furthermore, if the torsion spring 16 is metallic, then the end masses 12 and 14 must be electrically isolated from the spring 16 to avoid influencing the corrosion process through galvanic potentials generated by dissimilar materials in contact with each other and with the corrosive fluid.

Figure 4:
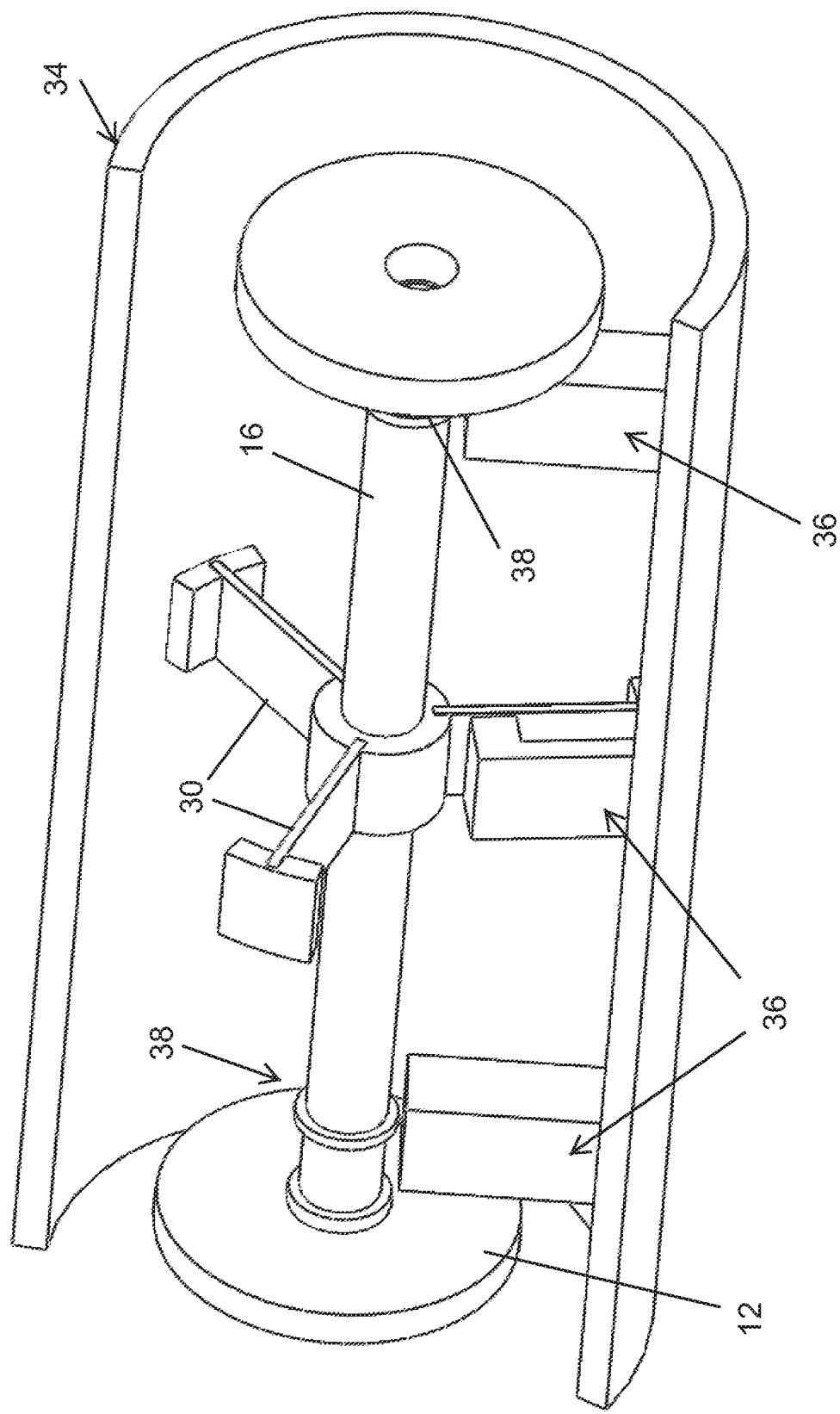
FIG. 4 shows a torsional resonator system in which the resonator is housed in a casing and supported in part by three leaf springs.

FIG. 4 shows a fourth preferred embodiment of the system in which the resonator is kept centered in a casing 34 by three leaf springs 30 disposed at equal intervals around the resonator, and excitation and sensing may be either continuous or intermittent. Magnetic transducers are used, with the appropriate excitation and sensing coils being disposed in pylons 36 extending radially from the casing. The necessary magnets and/or soft magnetic yokes are embedded in the rings 38 symmetrically disposed about the central hub. The casing may be built into a pipe, or it can be attached to a probe that can be inserted into a pipeline, wellhead, or other environment in which corrosion is to be measured.

A further preferred embodiment makes use of titanium components for all parts but the test disk. Titanium has the advantage of being resistant to corrosion by a wide variety of fluids. It is non-magnetic, and has a high electrical resistivity, so that the excitation, sense, and pickup coils will be little influenced by eddy currents. Hastelloy or other high nickel content alloy is another candidate for the system.

Figure 5:
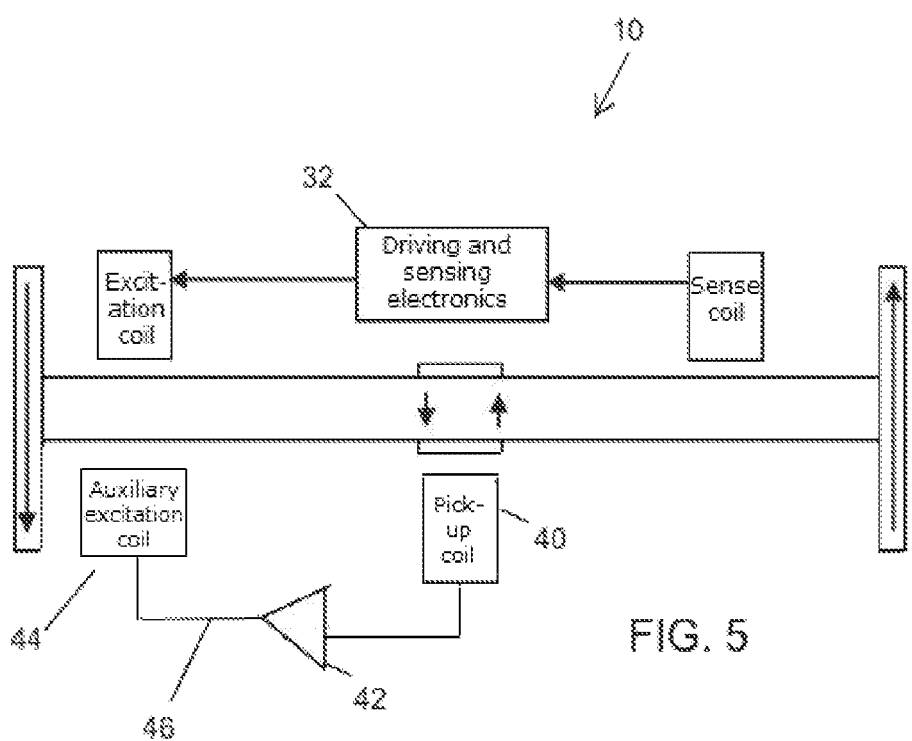
FIG. 5 is a diagram of a compensation measurement mode of operation for the system of FIG. 1.

Referring to FIG. 5, an alternative mode of operation for system 10 adds the advantage of a compensation measurement. In this mode, the output of the nodal pickup coil 40 is amplified by an amplifier 42 and fed back to an auxiliary excitation transducer 44. The system 10 is arranged so that the auxiliary excitation transducer 44 exerts sufficient torque on the end of the resonator on which the test disk is mounted to just balance the loss of inertial torque due to the loss of material through corrosion. The pickup coil voltage remains at zero, but the current 46 through the auxiliary excitation transducer 44 is a direct measure for loss of inertia of the test disk through loss of mass.

Figure 6:
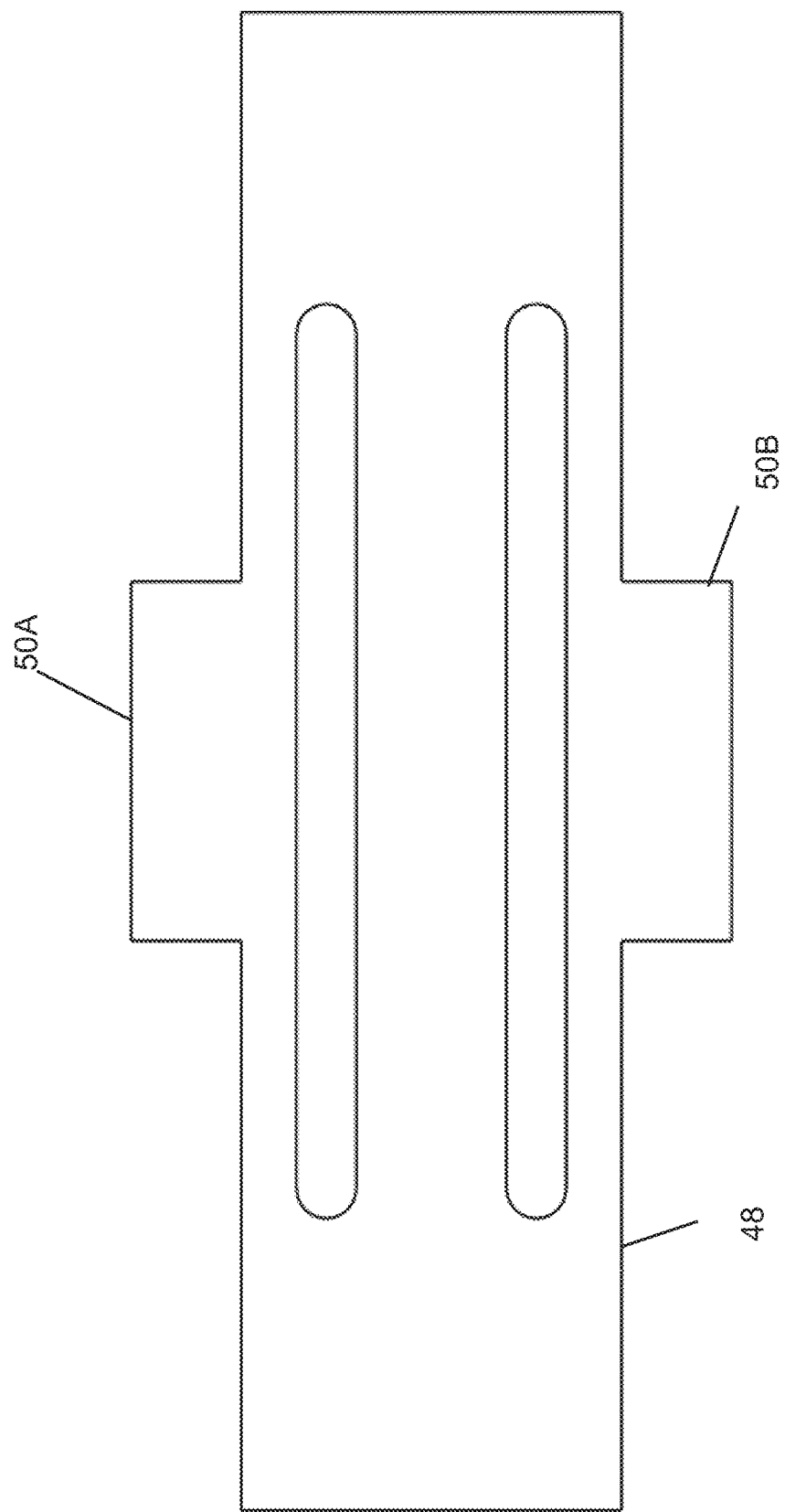
FIG. 6 illustrates a leaf spring with a cut-out pattern.
Figure 7:
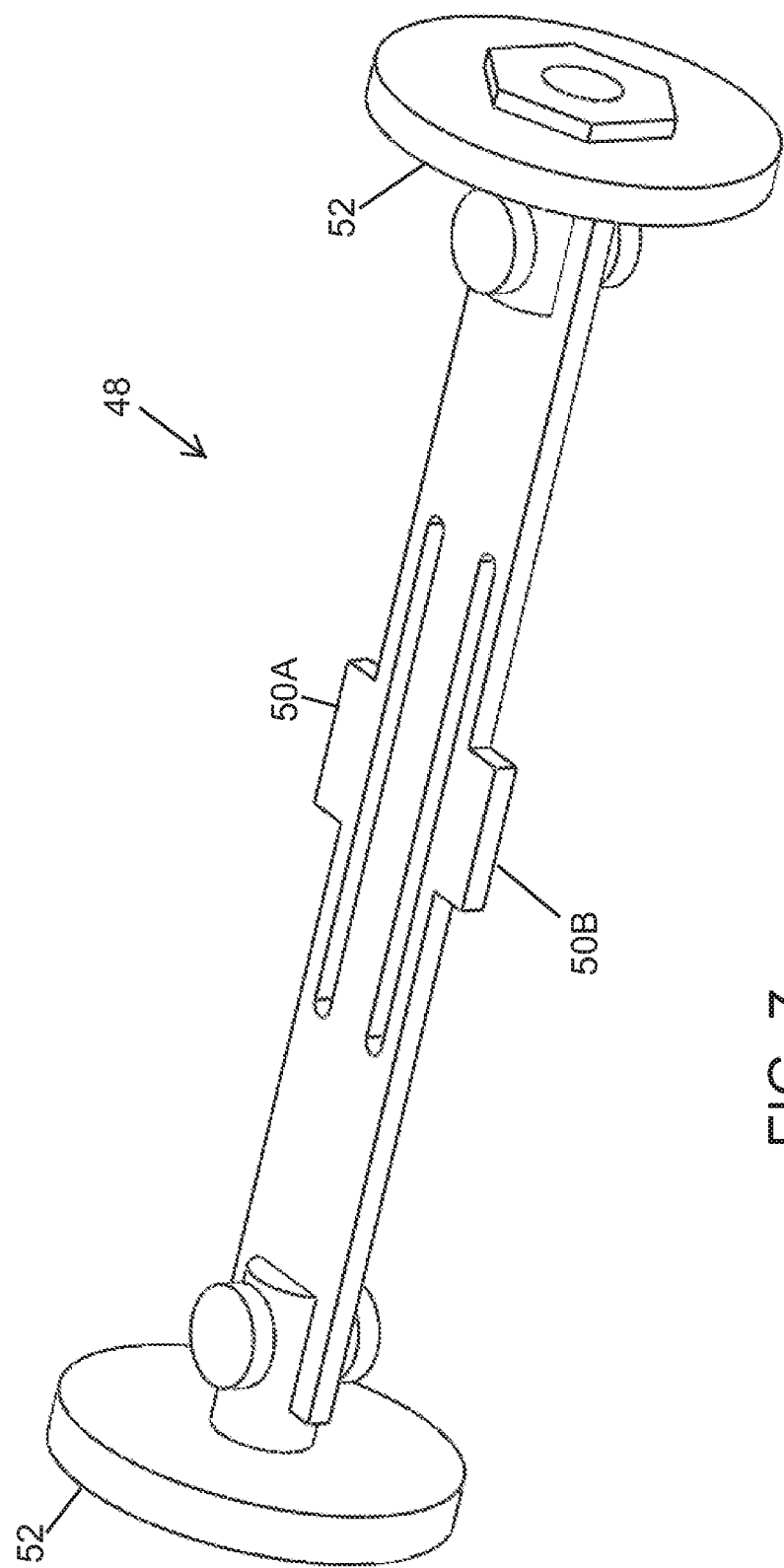
FIG. 7 shows a leaf spring structure with round corrosion test coupons.
Figure 8:
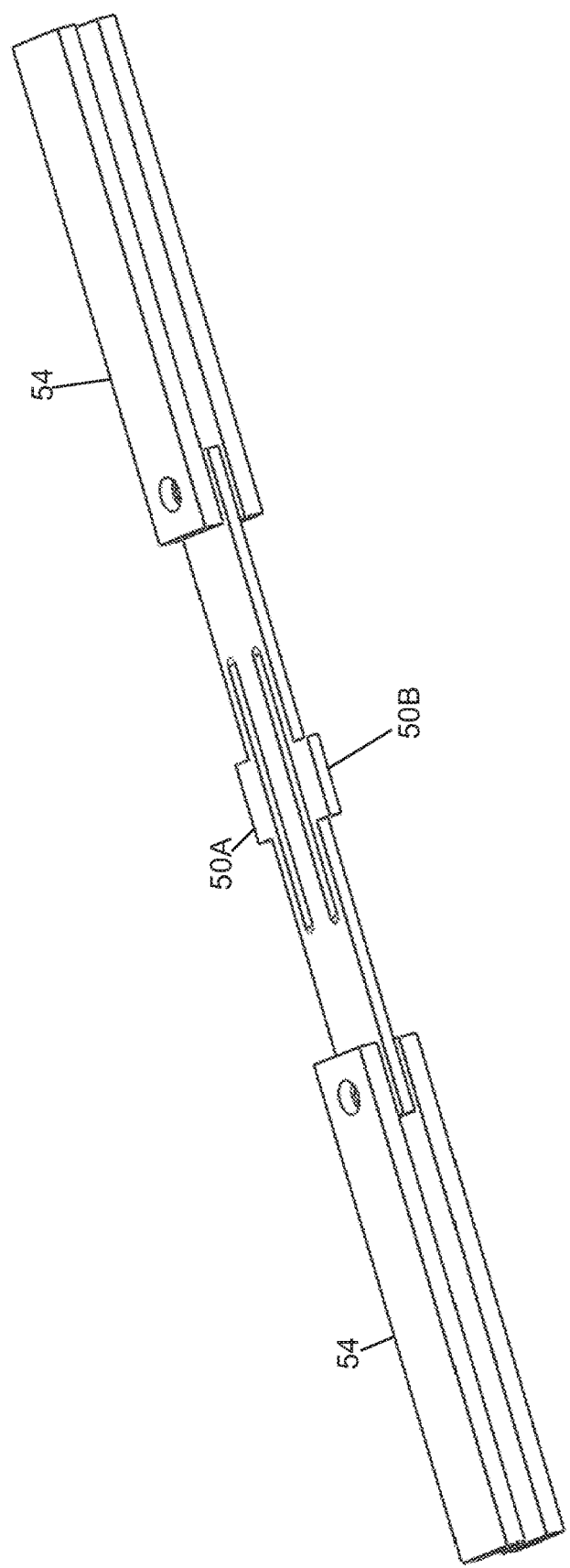
FIG. 8 shows a leaf spring structure with rectangular corrosion test coupons.

Other forms of symmetric resonators will work for this purpose. For instance, FIG. 6 illustrates a leaf spring with a cut-out pattern 48; its two ends and could be made differentially sensitive to corrosion (as by masking, selective deposition, etc.). The leaf spring 48 is anchored to the supporting structure by the upper 50A and lower tabs 50B. Alternatively, this leaf spring structure 48 could be used together with round 52 or even rectangular corrosion test coupons 54, as suggested in FIGS. 7 and 8, which are meant only to give the general idea of additional possible embodiments.

Figure 9:
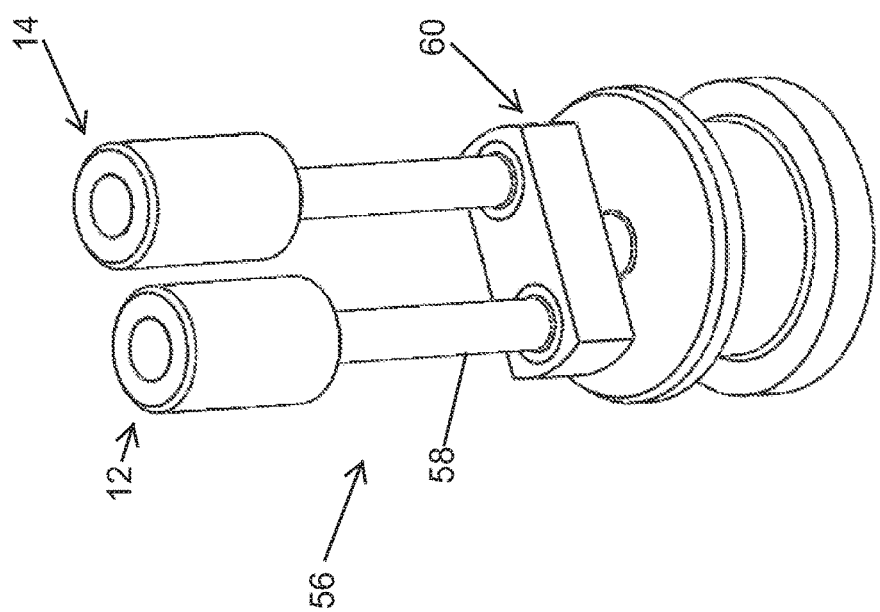
FIG. 9 depicts a compact corrosion measuring device consisting of a torsional tuning fork.

Finally, it is possible to use a torsional tuning fork, of which FIG. 9 is but one of many possible embodiments, as a compact corrosion measuring device 56. When the two tines 58 are balanced and vibrating in an anti-symmetric mode, the base experiences no torque. If the mass of one of the tines changes, the tuning fork becomes unbalanced, and a net torque is exerted on the base 60, which will oscillate in much the same way as the nodal leaf springs 30 and 48 did in the previously disclosed embodiments.

Any and all of these embodiments can be used for measuring corrosion. For instance, the two inertial masses may be provided with different coatings to measure variability in corrosion, and the same measurement principles used to monitor the differential mass change between the test and reference masses 14 and 12. Alternatively, the test mass 14 may be clad or plated or otherwise coated with a substance whose behavior in a given fluid is to be monitored.

An important advantage of these systems is that they are completely immersed in the fluid, and thus in thermal equilibrium with it. If one end of a symmetric resonator were to be brought to a different temperature than the other end, it would become unbalanced because of the inequality of the spring constants of the two ends of the torsion spring 16. In comparison to prior art systems, which rely on measurements of the frequency response of a resonator from which mass may be removed by corrosion, the frequency is of no particular interest in this system; it is only important that the resonator be excited at its appropriate resonant frequency, even though this frequency will change in response to temperature variations and changes in mass loading.

Figure 10:
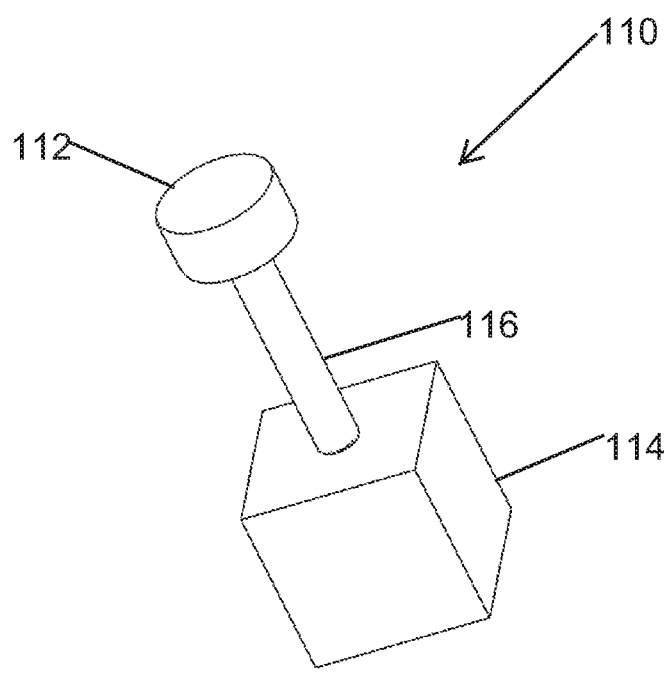
FIG. 10 shows a generalized depiction of a resonator that can be used in a method, according to the present invention.

An additional preferred embodiment is also based the effect of corrosion on an electromechanical resonator. Referring to FIG. 10, a mass-spring torsional resonator 110 includes a cylindrical mass 112 coupled to a nodal mass 114 by a tubular torsion spring 116. The resonant frequency of resonator 110 depends on the mass of mass 112 and the spring constant of spring 116.

The frequency of this resonator is determined by the equation:

$$F = \frac{1}{2\pi}\sqrt{\frac{G}{I}}$$

where F is the resonant frequency of the resonator, G is the torsional stiffness of the torsional spring 116, and I is the moment of inertia of the mass 112 about the longitudinal axis of the resonator.

A first method for using resonator 110 to monitor corrosion is to make the mass out of a material that is resistant to corrosion in the fluid environment of interest, while making the spring 116 from the same material as the equipment whose corrosion is to be monitored. As the corrosive fluid attacks the spring 116, it becomes thinner, decreasing its stiffness, and lowering the resonant frequency of the resonator 110. Since the resonant frequency is directly related to the spring constant, and since the spring constant is dependent on the thickness of the torsional spring 116, the decrease in the resonant frequency can be directly related to the amount of material lost from the spring.

Two factors affect the accuracy of this method, the first being the effects of temperature on the resonator's resonant frequency. The torsional stiffness of the spring is linearly dependent upon the shear modulus of the spring's material, and the shear modulus is, in turn, dependent on the temperature of the material. Since the temperature coefficient of the shear modulus may be determined experimentally, and is a property of the torsion spring material, it is possible to control and/or compensate for the frequency change of the resonator due to temperature effects.

Figure 11:
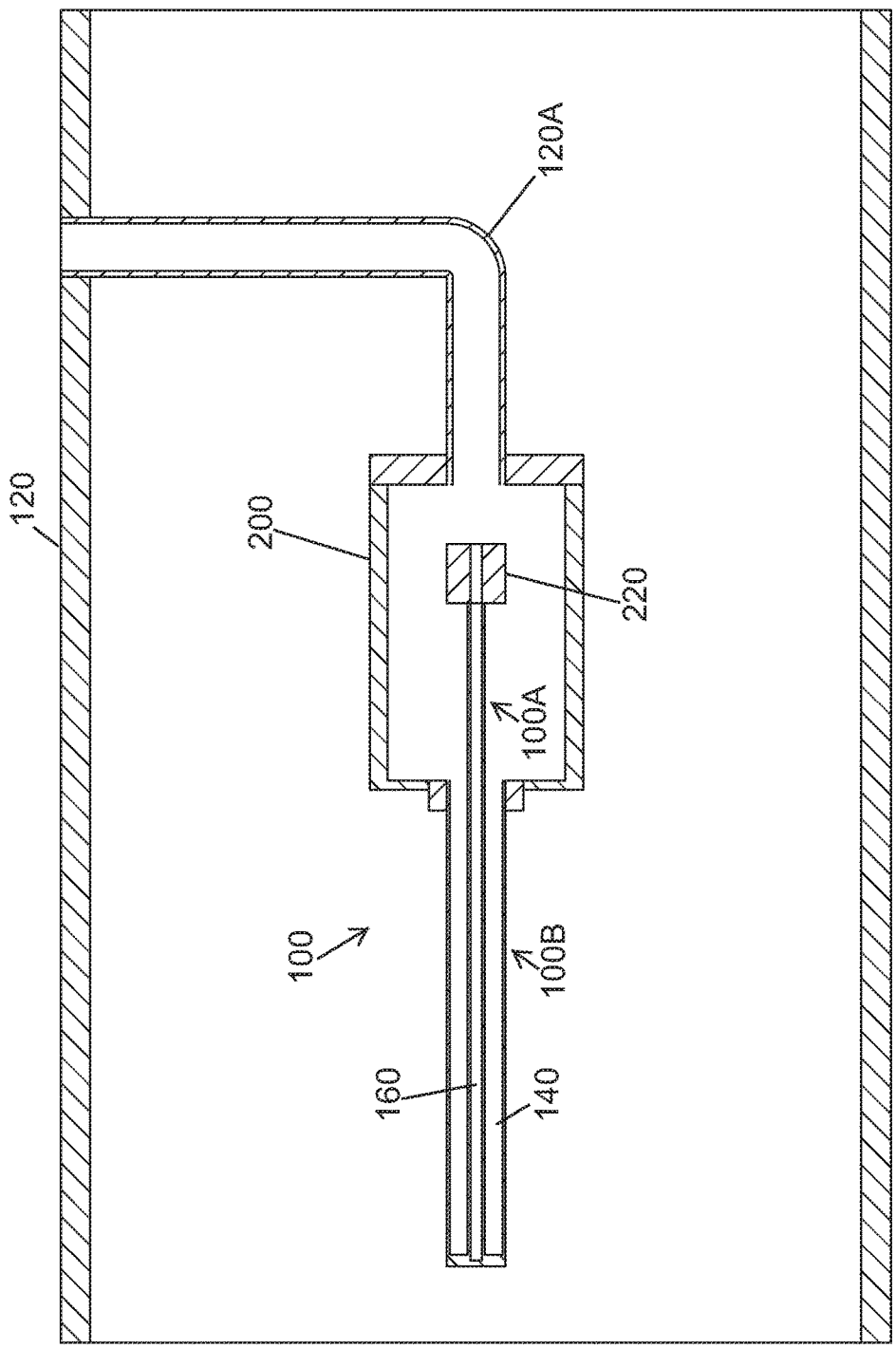
FIG. 11 is a sectional view of a transversely vibrating resonator mounted on one end of a bent pipe.

Referring to FIG. 11, which shows a first preferred embodiment, a housing 200, supporting a transversely vibrating resonator 100 is mounted on one end of a bent pipe 120A. Bent pipe 120A is preferentially made of a thermally insulating material; consequently, in holding the sensor completely immersed in the fluid, the pipe ensures that both the exposed part of the resonator and the housing of the sensor reach equilibrium with the temperature of the fluid. The resonator 100 is essentially isothermal, with enclosed portion 100A approximating the temperature of the exposed portion 100B, so that its unloaded resonant frequency can be determined as long as the temperature of the fluid is known. The support pipe 120A is also used as a conduit for electrical connections to the transducer element 220 affixed to the free end of the inner rod 160 of the resonator 100. The entire transducer also includes an additional element (not shown) that exerts a force upon element 220, exciting the resonator in a torsional mode, and also sensing the resonator's rotational vibratory motion. In a preferred embodiment transducer element 220 is a permanent magnet, which is driven by an electromagnet assembly (not shown) mounted in housing 200. Because the outer tube (also being a torsional spring) 140 vibrates torsionally, or in an alternative embodiment, transversely, corrosion of spring 140 changes the spring characteristics and changes the resonant frequency of resonator 100. By determining the change in resonant frequency over time, a measurement or estimate can be made of the amount of corrosion of tube 140. Because the resonator 100 is kept at a uniform temperature it is easier to form a measurement of the resonant temperature, thereby making it possible to separate the effects of temperature (from a temperature measurement device that is not shown) at the moment from corrosion that has changed the spring characteristics of spring 140.

Figure 12:
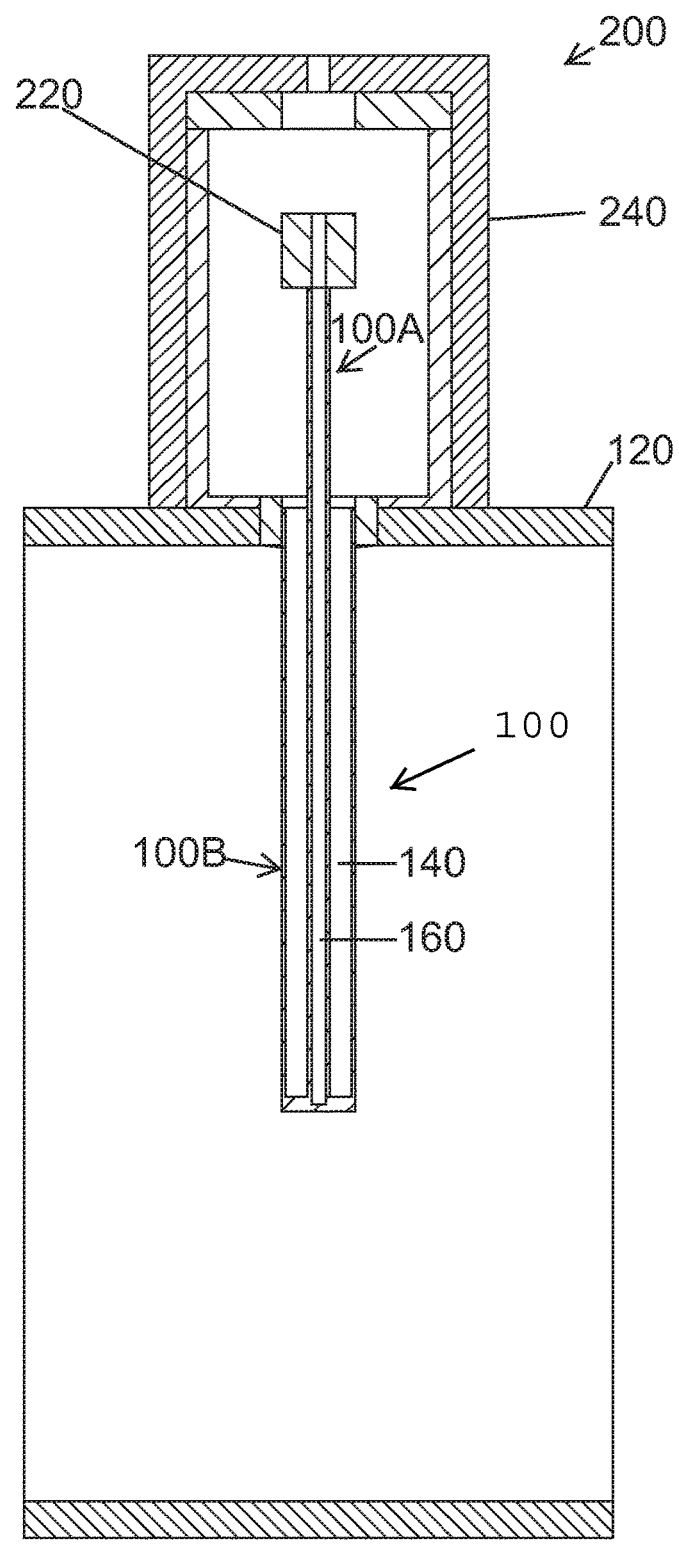
FIG. 12 is a sectional view of a transversely vibrating sensor mounted radially in a pipe.

Alternatively, a transversely vibrating sensor may be mounted radially within a pipe 120, as shown in FIG. 12, which illustrates a second preferred method. Those parts of the body of the sensor not in immediate contact with the fluid are covered by a high-efficiency insulating sheath 240, which renders the covered parts of the sensor essentially adiabatic. Since heat is neither lost nor gained by the enclosed part 100A of the resonator, all of its parts eventually come into equilibrium with the exposed portion 100B, making the resonator isothermal with a temperature equal to that of the fluid. Similar to the previous embodiment, a uniform temperature permits an easier measurement of temperature by a measurement device (not shown).

Figure 13:
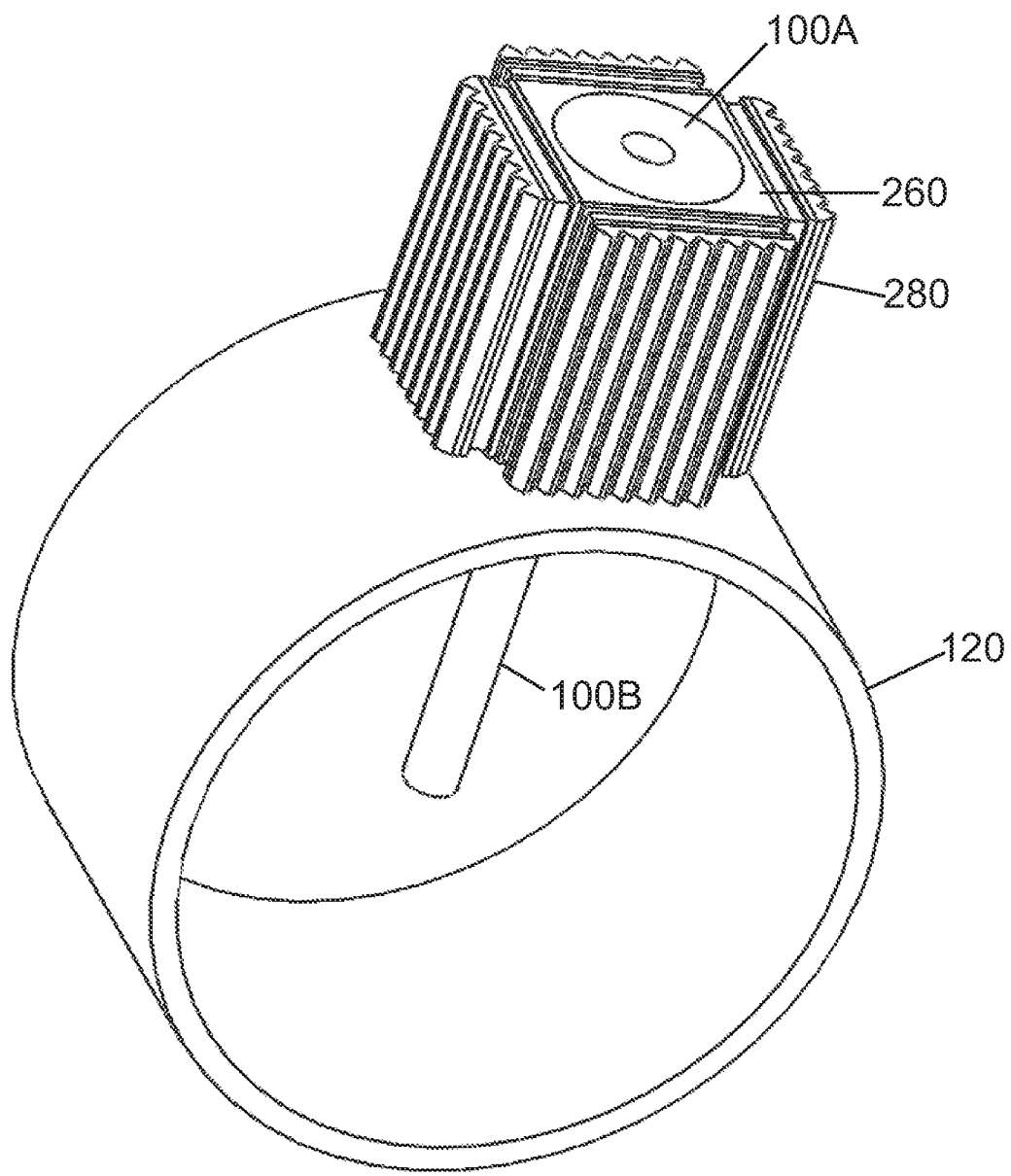
FIG. 13 is an isometric view of the transversely vibrating sensor of FIG. 3 surrounded by a thermally conductive block and Peltier devices, respectively.
Figure 14:
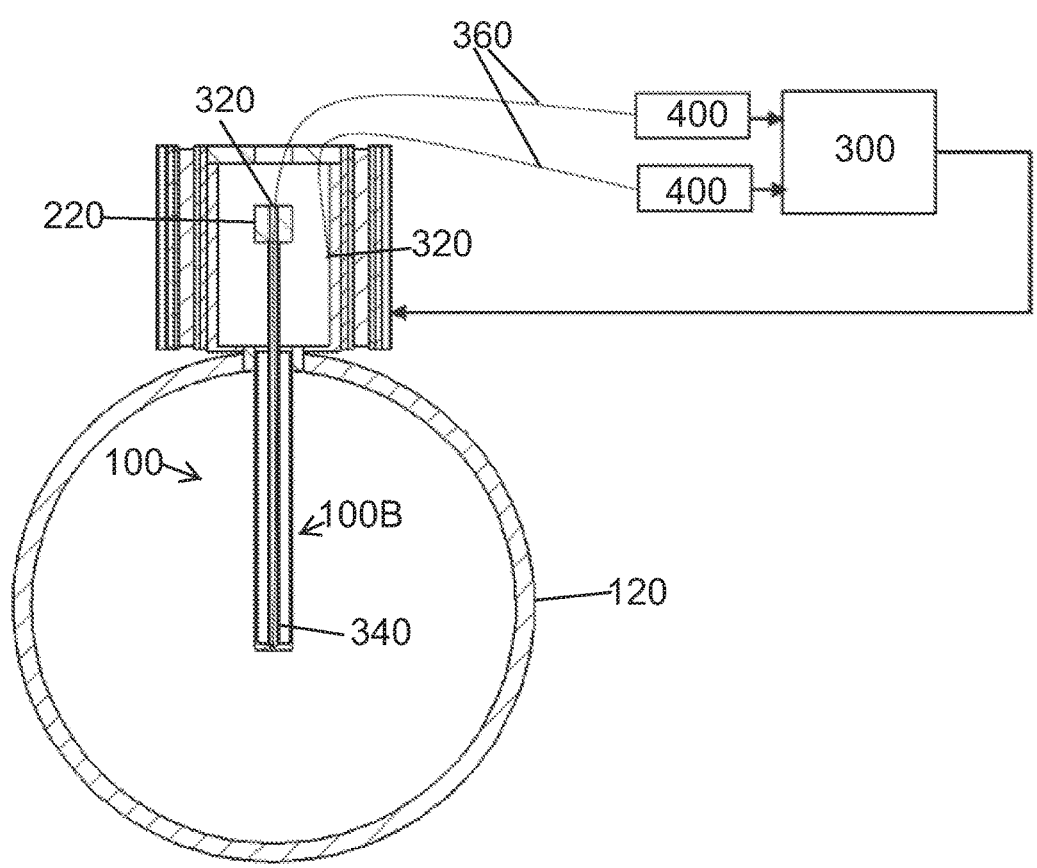
FIG. 14 is a sectional view of the transversely vibrating sensor of FIG. 4, showing the paths to the thermocouples and controller.

In a third preferred method, shown in FIG. 13, which may be used either alone or in combination with one of the presently described methods, the non-immersed portion of resonator housing 200 possesses means for heating and/or cooling the portion of the housing. The enclosed portion of sensor 100A is surrounded by a thermally conductive block 260, in turn surrounded by an array of Peltier devices 280, which are connected to appropriate power supply and control means 300 capable of maintaining the sensor body at a preset temperature (as shown in FIG. 14.). These temperature regulation means accept a temperature measurement from a model or a temperature sensor located in the exposed portion 100B of resonator 100, and calibrates adjusts the temperature of the non-immersed portion of resonator housing 200 to the temperature of the immersed portion of the resonator 100. The two temperatures are compared, and their difference is used as the error signal for a controller 300 that adjusts the power input to the Peltier heater/cooler so as to drive the temperature difference to zero. These temperature regulation means together with the heating and/or cooling means constitute a system for maintaining the resonator 100 in an isothermal condition. This process causes the resonator 100 to become essentially isothermal. In alternative embodiments, other types of heating and cooling devices, other than Peltier devices, are used. In this embodiment, the temperature of resonator 100 is known and is used to compensate for the effect of temperature on the shear modulus of resonator 100, so that a more accurate measurement of corrosion over time can be formed.

The accuracy of the first preferred method is based on the assumption that the thermal conductivity of the non-immersed end of the sensor is sufficiently high and that its heat transfer to surrounding structures is sufficiently low to ensure that the resonant element is isothermal. Similarly, the accuracy of the second preferred method is based on the assumption that the heat conductivity of the thermal insulation surrounding the housing protecting the non-immersed portion of the sensor is sufficiently low, that its temperature is substantially the same as that of the immersed end of the resonator 100. Similarly, the accuracy of the third preferred method depends on the efficacy of the Peltier heating/cooling system to maintain the body at the same temperature as the fluid end of the resonator 100.

Figure 15:
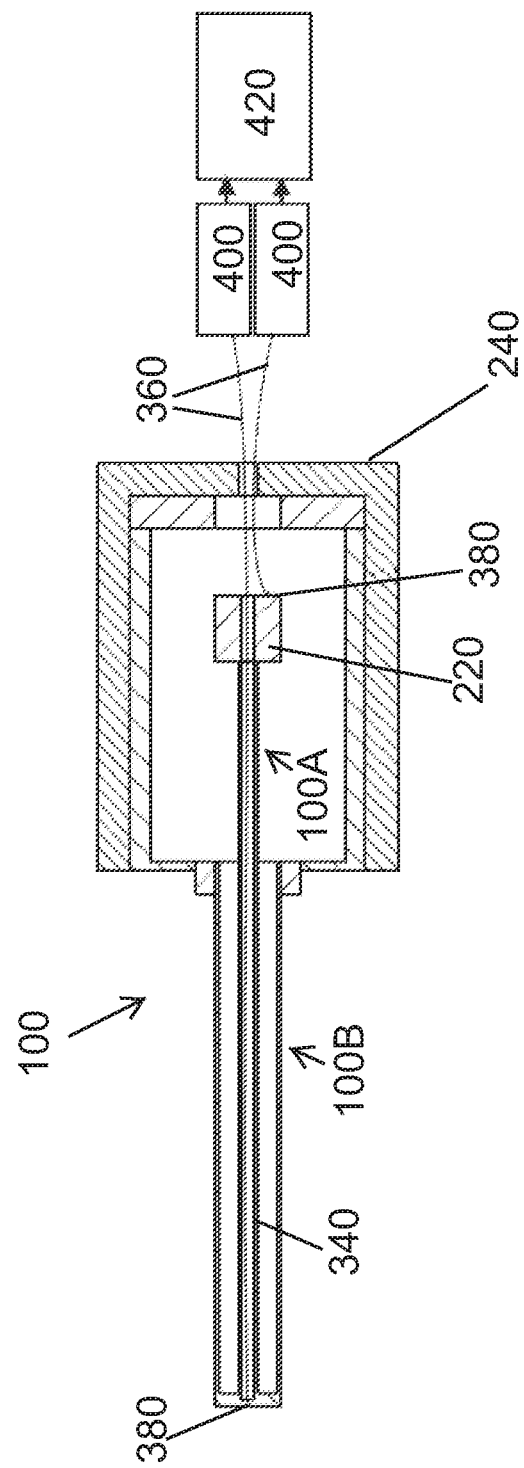
FIG. 15 is a more detailed sectional view of the sensor of FIG. 53, showing the disparate locations of two thermocouples.

A fourth preferred method, illustrated in FIG. 15, which may be used either alone or in combination with one of the presently described methods, consists of providing means to measure the temperatures of at least two locations within resonator 100, and providing a model to predict the unloaded resonant frequency of the resonator based on the measured temperatures of at least two locations within resonator 100. In one variant, based on the first preferred method, housing 200 is preferentially includes thermally insulating material 240, and at least two temperature sensors 320 are placed at at least two locations on the sensor, typically at the tip and the transducer end. In a preferred embodiment, the inner rod is replaced by a hollow tube 340, to permit conducting the leads for the temperature sensor to the free end of the resonator. The transducer is also provided with a through hole to permit the exit of the temperature sensor leads 360. Similarly, a second temperature sensor 320 is attached to the transducer end of the resonator. The temperatures measured from at least two locations within resonator 100 are used in a predictive model to correct for imperfections in the measures used to make the sensor's resonator isothermal. In a preferred embodiment, the temperature sensors are thermocouples 380, as these can be fabricated from very fine wire whose mass and rigidity are negligible compared to the resonator's, and thus have negligible influence on either the resonator's frequency or damping. The two thermocouples' outputs are amplified by the thermocouple amplifiers (TC amp) 400 and serve as inputs to an algorithm stored in the processor 420 which predicts the unloaded frequency of the resonator (FIGS. 14 and 15). Further, the predictive model and the measured temperatures of at least two locations within resonator 100 are used by an algorithm to predict the corrosion of the tube 140 by the fluid given the change in resonant frequency of the resonator 100. The better the initial isothermal condition of the resonator, the more accurate the compensation by this method. This computational method for correcting residual departures from isothermal conditions may equally well be applied to the second or third preferred methods described above to improve its accuracy. Similar to the previous method, knowledge of the temperature permits separation of sheer modulus of tube or spring 140 due to temperature, versus due to corrosion, thereby forming a better measurement of corrosion over time.

It is further understood that the two-point temperature measurement is merely illustrative of a more general compensation method. In cases where a two-point measurement does not provide sufficient accuracy, it is possible to use three or more measurements together with suitable models for temperature distribution in the resonant sensor. Additionally, it is further understood that, although the sensors in the foregoing embodiments were shown with generic transducers, the transducer means may be selected from the group of piezoelectric, capacitive, electromagnetic, magnetostrictive, optical, or any other transduce means capable of exciting the desired resonance in the resonator, and/or of measuring the resonant response of the resonator.

The foregoing embodiments make use of a coaxial bending resonator. However, any resonator may be used provided it vibrates perpendicular to its own surface over at least part of its surface. In the following descriptions of preferred embodiments, it is to be understood that these all can be rendered nominally isothermal using the techniques of immersion and/or insulation described above, and that the accuracy of the immersed and/or insulated sensor can be enhanced by means of the temperature measurement and compensation scheme described in the foregoing section.

Bending resonators that vibrate transversely, such as the one described above, have the disadvantage of being vibrationally unbalanced. As the tubular section vibrates, it exerts substantial reaction forces on the resonator's body, which may give rise to energy leakage into the supporting structures—which, in turn, introduces uncertainty into both the unloaded resonant frequency and the unloaded damping of the resonator. In another preferred embodiment, the resonant sensor consists of a balanced resonator, in which two coupled resonant elements are joined together in such a way that the reaction forces on their common mounting are largely neutralized, resulting in superior isolation from mounting influences compared to an unbalanced resonator. A common tuning fork is an example of a balanced bending resonator. Prior art teaches the use of both bending and torsional immersed tuning forks to measure fluid properties. These have the disadvantage, however, of being difficult to drive and sense without also immersing the transducer(s) in the fluid being measured.

Figure 16:
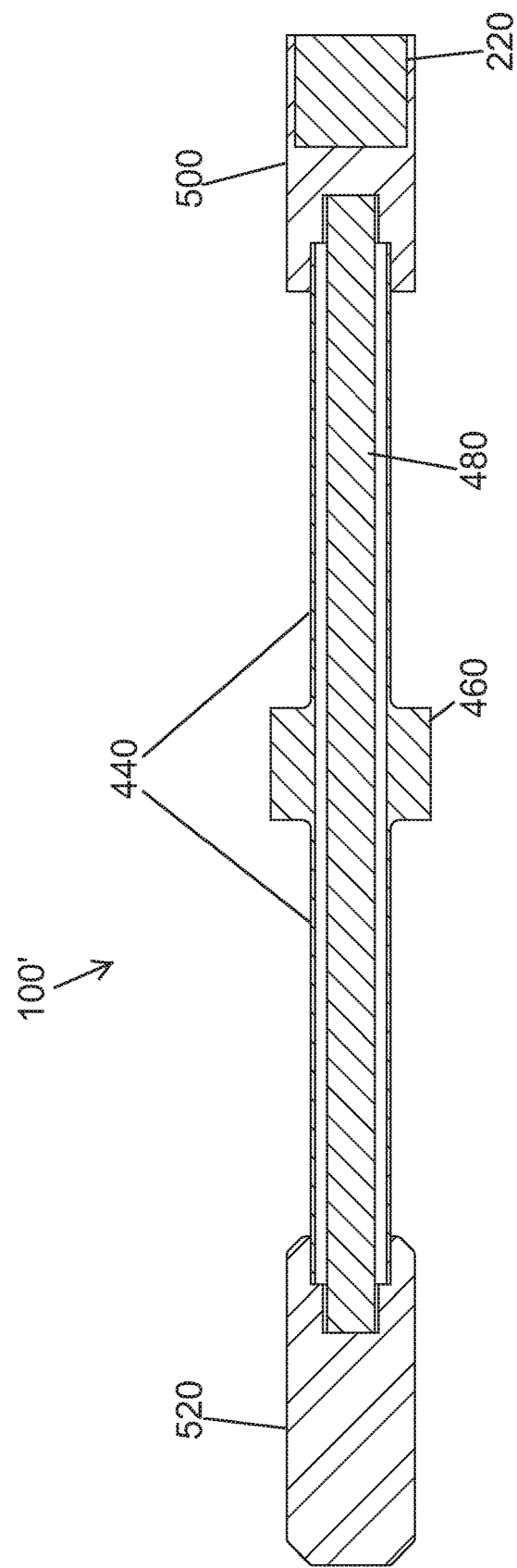
FIG. 16 shows a sectional view of a symmetrical resonator having a fluid end mass and a transducer end mass mounted on a coupling rod.

Another kind of balanced resonator that does not have these disadvantages is disclosed in U.S. Pat. No. 9,267,872. Referring to FIG. 16, balanced resonator 100' consists of a torsion spring in form of a tube 440 symmetrically configured about a nodal hub 460. Coupling rod 480 joins the transducer end mass 500, driven in torsion by transducer means not further described here, and the fluid end mass 520. The fluid end mass 460 is dimensioned so as to have the same moment of inertia as the transducer end mass 500, so that the entire assembly vibrates as a symmetrical resonator, the desired mode being that in which the two ends twist in opposite directions. When vibrating in this mode, there is no net torque exerted on the nodal hub.

In order to measure corrosion with this symmetric torsional resonator, it is necessary to know its resonant frequency when it is not loaded by fluid. This unloaded resonant frequency is, as is the case with all resonators disclosed in this application, dependent on the temperature of the resonator. And as in the other resonators, unless the resonator is isothermal, it is difficult or impossible to predict its unloaded resonant frequency with good accuracy.

Figure 17:
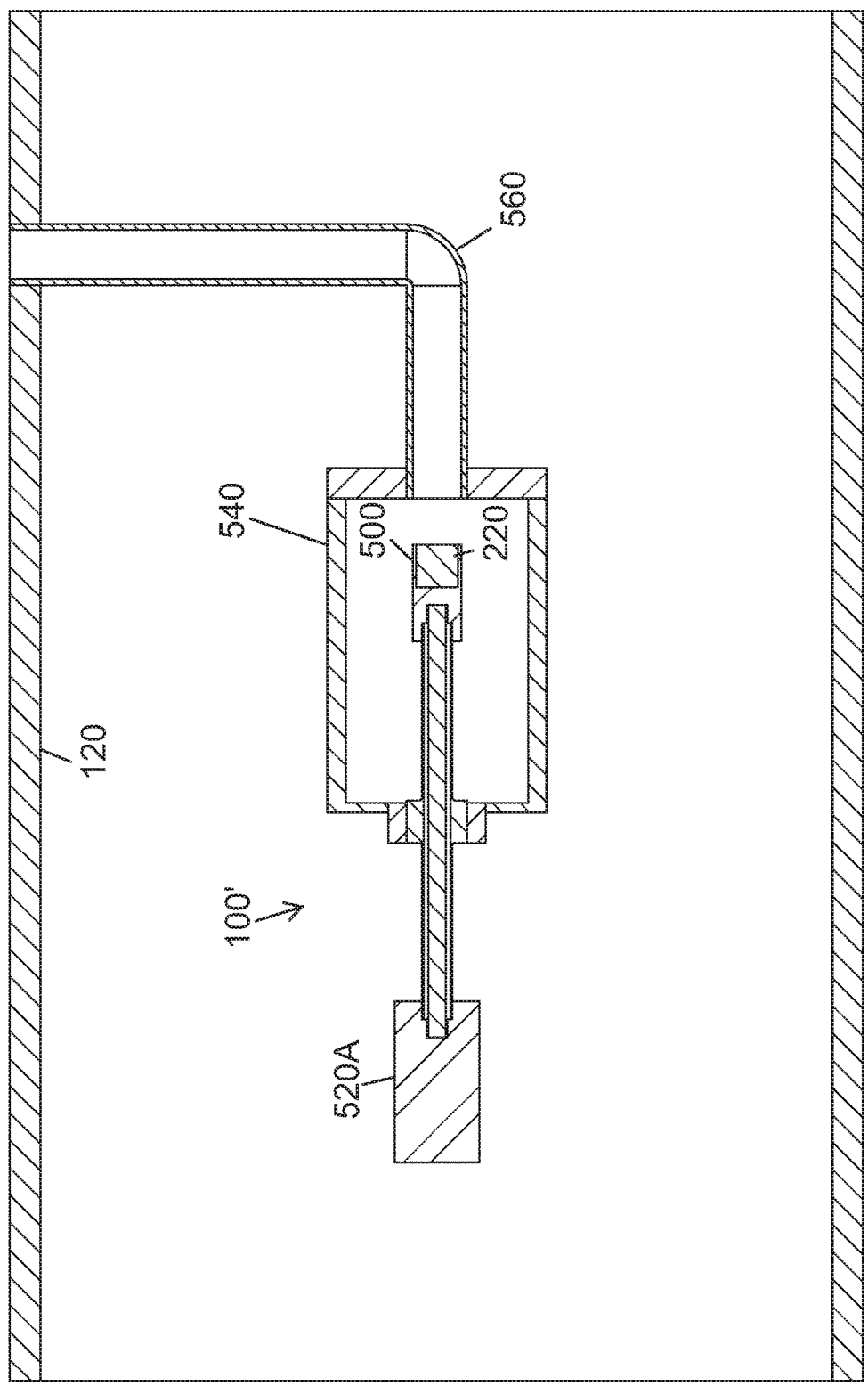
FIG. 17 is a sectional view of a symmetric resonator with its transducer end enclosed in a thermally conductive body, attached to the wall of a pipe by a thermally-insulating support, and having a flattened fluid end mass.

FIG. 17 shows a symmetric torsional resonator 100' with its transducer end enclosed in a thermally conductive body 540, attached to the wall of a pipe 120 by a thermally insulating support 560. This renders the entire resonator essentially isothermal, although it is understood that in cases where there is a minor temperature difference between the fluid end mass 520 and the transducer end mass 500, an additional temperature compensation step may be implemented in the methods described above, where temperature sensors are used to measure the actual temperatures at both ends of the resonator and this information used to calculate a correction factor for the unloaded resonant frequency of the resonator.

This configuration is particularly favorable for use in devices to measure corrosion downhole in oil and gas production since the environment downhole is typically isothermal.

Figure 18:
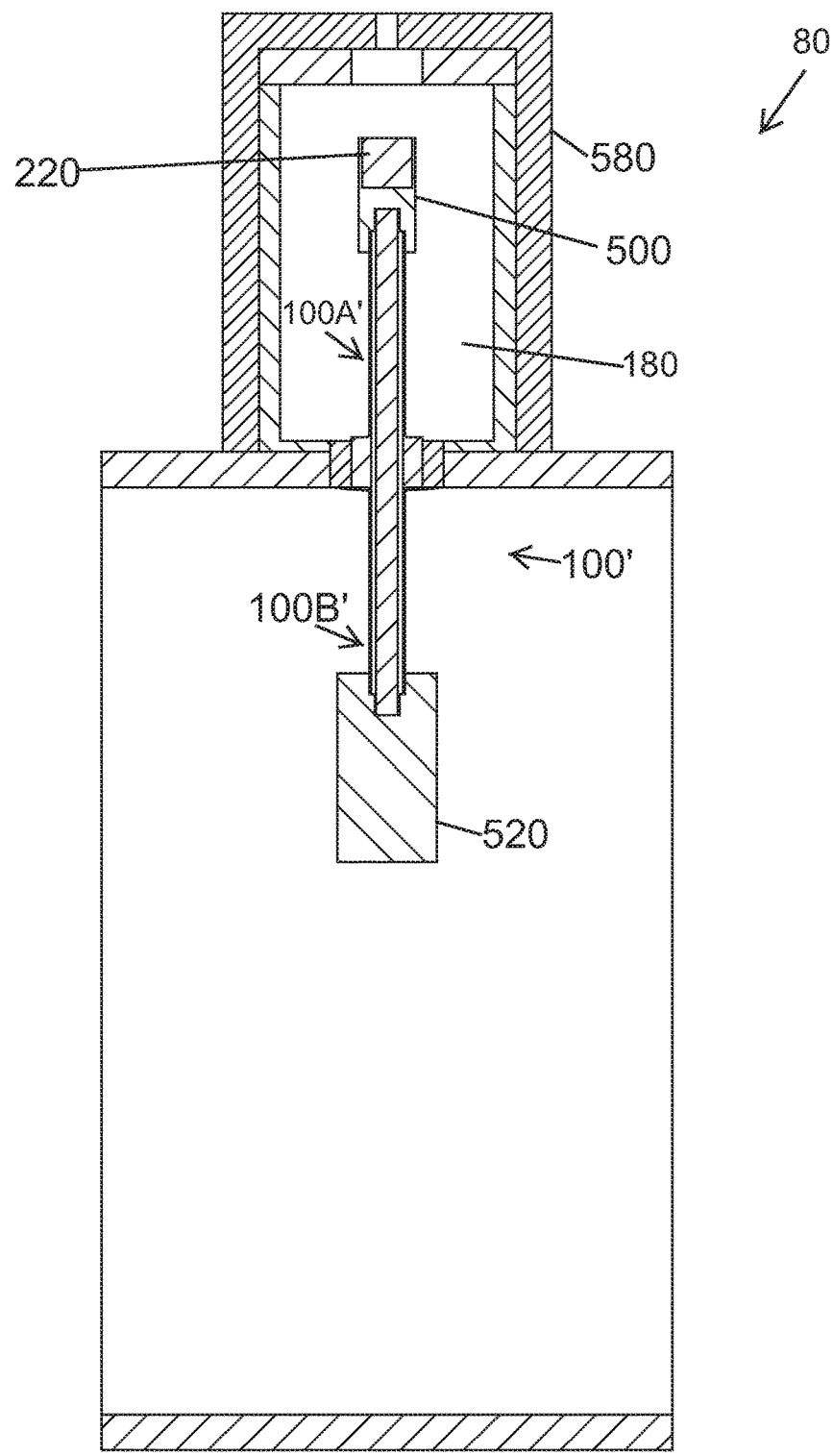
FIG. 18 is a sectional view of a symmetric torsional resonator with a flattened fluid end mass, with a thermally insulating sheath surrounding its transducer end mass.

Referring now to FIG. 18, a preferred embodiment of a corrosion monitoring device 80, includes a symmetric torsional resonator 100' that is shown with a flattened end 520. Also, a thermally insulating sheath 580, surrounding a housing 540, which defines a chamber 180. As in FIG. 12, the sheath prevents thermal exchange with the ambient environment, keeping the symmetric resonator essentially isothermal with the fluid temperature. This embodiment may further include the temperature measurement elements shown in FIG. 15, so that, minor temperature differences between the enclosed portion 100A' and the exposed portion 100B' may be measured, and the temperature difference used to algorithmically compensate for the temperature difference. It is further understood that the insulating sheath may be replaced by the heating/cooling system as shown in FIGS. 13 and 14 with substantially the same function when applied to the system of FIG. 18. A second factor affecting the accuracy of the method is the possibility of corrosion measurement artifacts being generated by electrochemical potentials caused by differences of electronegativity of the materials of which each element of the resonator is made. At least two methods are available for correcting for such artifacts. The first is to make all of the components from the same material. Since that would render all components vulnerable to corrosions, the components can be covered by a fluid-excluding coating, such as teflon, epoxy-based paint, diamond like coating, or a similar impermeable coating that is resistant to attack by the target fluid. A second method is to use corrosion-resistant materials for the non-spring components, but to ensure that these corrosion-resistant materials have the same electronegativity as the spring material.

Further aspects of this invention disclose preferred embodiments of this method, specifically designs for resonant systems that fulfill the basic requirements of the method while embodying devices that are convenient for use in typical corrosion-monitoring environments.

These fall into two broad categories. A first category consists of resonators that permit differential measurements. They consist of two resonators, either separate or coupled, that are exposed to the same fluid, are maintained at the same temperature as one another, but differ in the corrodibility of their measurement elements, which, as described earlier, can be either their masses or their springs. A second category consists of resonators whose non-corroded frequency is calculated by computational means, based on one or more temperatures measured on or in the immediate vicinity of the resonators, the non-corroded frequency being used as a reference to calculate the degree of corrosion from the frequency of the corroded resonator.

This resonator may be either single ended, or preferably a symmetric resonator as disclosed in U.S. Pat. No. 9,267,872, issued Mar. 23, 2016. Resonators that are constructed according to one of the methods disclosed herein, namely, that one of the two resonators has either a spring or a mass that is corrodible, while the second resonator is constructed so as to be relatively non-corrodible. In that case, the frequency of the non-corrodible resonator is compared to that of the resonator with a corrodible element, a degree and rate of corrosion being calculated from the difference in resonant frequency.

A second broad category of devices embody the methods described above for maintaining a single non-differential resonator at a substantially constant temperature so that the non-corroded frequency can be calculated from one or more temperature, see above, text describing FIG. 15. One particularly advantageous embodiment uses a completely immersed torsional tuning fork of the type described in Published Application No. 2013/0139576, published on Jun. 6, 2013, which discloses a fluid properties resonator particularly adapted to downhole use at high temperatures and pressures. By modifying the torsional tuning fork design so that either the masses or springs are made of corrodible materials, the tuning fork can be used to monitor corrosion by one of the methods disclosed above.

It is possible that while using any of the foregoing methods or devices, that large changes in fluid properties, including but not limited to any combination of density and viscosity, could cause changes in the resonant frequency of the resonator unrelated to corrosion of the resonator or its parts. A method for compensating for such fluid properties changes uses an auxiliary sensor located near the corrosion sensor, the parts of the auxiliary sensor in contact with the fluid being made of a material immune to corrosion by the target fluid. The auxiliary sensor provides input to a data processing device executing a program that implements a computational algorithm that compensates the corrosion measurement for the effects of fluid properties on the resonant frequency of the corrosion monitoring device.

In an alternative method, analysis is performed based on measurements of temperature and damping of the single corrosion-sensitive resonator to compensate for the effects of changes in fluid properties.

A comparison of the resonant frequency of a resonator, such as resonator 100 or 100', from one point in time to another, yields a measure of the corrosion that has taken place between those two time points. If the first time point is the resonator installation, than the second time point measurement yields total corrosion during the time period since resonator installation. In one preferred embodiment, the resonator is replaceable within the corrosion measurement device. A log of values may provide a history of corrosion over time, which may be quite valuable in situations where a changing progression of fluid is passing by the resonator. For example, the characteristics of crude oil from a particular well may change over time. Even a stream of fluid in an industrial plant may show some variation. In some situations it may be valuable to know when the greatest corrosion was occurring.

INDUSTRIAL APPLICABILITY

The present invention finds industrial applicability in the field of manufacturing fluid property measurement devices and in the monitoring of fluid properties and/or effects of fluids on surrounding structures.

The invention claimed is:

1. A method of measuring the amount of corrosion of a target material caused by exposure to a fluid, over a period of time:
   a. providing a corrosion measuring device comprising:
      i. a torsional resonator having a first surface area made of a material having a corrosion profile like that of said target material and having a second surface area made of material having a corrosion profile unlike that of said target material;
      ii. a transducer assembly, positioned to drive said resonator in torsion and sense resultant resonator torsional motion, thereby producing a sense signal;
   b. exposing said resonator to said target fluid over said period of time and analyzing said sense signal over said period of time to determine changes in how said resonator responds to being driven torsionally by said transducer assembly, over time.

2. The method of claim 1 wherein said first surface area is made of said target material.

3. The method of claim 1, wherein said torsional resonator has a resonant frequency and said analyzing of said sense signal determines if said resonant frequency has changed over time.

4. The method of claim 3, wherein said torsional resonator includes a first resonator mass, having said first surface area and a second resonator mass, having said second surface area, and wherein both resonant masses are immersed in said target fluid, different corrosion of said two resonant masses causing a change in resonant frequency.

5. The method of claim 3, wherein said resonator has two resonant masses, collectively having said second surface area, and being joined by a torsional spring having said first surface area, and wherein corrosion of said torsional spring causes a change in resonant frequency.

6. The method of claim 5, wherein said device further includes a fluid-impervious housing and wherein a first one of said resonant masses is enclosed in said housing and a second one of said resonant masses is exposed and wherein said step of exposing said resonator to said target fluid includes exposing said second mass and at least a portion of said torsional spring to said target fluid.

7. The method of claim 6, wherein said resonator is maintained in a state where said exposed mass and said enclosed mass are kept at an average temperature that is less than 5° C. separate.

8. The method of claim 6, wherein temperature of said resonator is measured at two displaced points, and wherein said measurements are utilized in arriving at a corrosion measurement.

9. The method of claim 1, wherein said target material is carbon steel.

10. The method of claim 1, wherein a log of readings is recorded and analyzed to provide a history of corrosion over said time period.

11. The method of claim 1, wherein said time period is greater than a week.

12. The method of claim 1, wherein said time period is greater than a month.

13. The method of claim 1, wherein said time period is greater than a year.

14. The method of claim 1, wherein a companion sensor assembly measures a fluid property set, and said measurements are compared to arrive at a corrected measurement of tendency of corrosion of said target material.

15. The method of claim 14, wherein said fluid property set includes one or more properties taken from a set consisting essentially of density, viscosity, electrochemical potential and ph.

16. The method of claim 1, wherein said resonator is a symmetric resonator and said transducer assembly senses movement of a nodal point away from an original location, and said sense signal reflects said location of said nodal and said analysis uses said nodal point location in determining extent of corrosion of said first surface.

17. The method of claim 16, wherein said transducer assembly is responsive to said sense signal to return said location of said nodal point to said original location.

18. The method of claim 1, wherein said analysis of said sense signal yields a measure of damping which in turn, yields an estimate of roughening of said first surface due to corrosion.

19. A corrosion measuring device for measuring the tendency of a target fluid to corrode a target material, comprising:
   a. a torsional resonator having a first surface area made of a material having a corrosion profile like that of said target material and having a second surface area made of material having a corrosion profile unlike that of said target material;
   b. a transducer assembly, positioned to drive said resonator in torsion and sense resultant resonator motion, thereby producing a sense signal;
   c. a data processing assembly adapted to receive said sense signal and analyze it to determine a change in resonator response to being driven in torsion by said transducer assembly.

20. The device of claim 19, wherein said first surface area is made of said target material.

21. The device of claim 19, wherein said resonator has a resonant frequency and said analyzing of said sense signal determines if said resonant frequency has changed over time.

22. The device of claim 21, wherein said resonator includes a first resonant mass, having said first surface area and a second resonant mass, having said second surface area, and wherein both resonant masses are immersed in said target fluid, different corrosion of said two resonant masses causing a change in resonant frequency.

23. The device of claim 21, wherein said resonator has two resonant masses, collectively having said second surface area, joined by a torsional spring, having said first surface area, and wherein corrosion of said torsional spring causes a change in resonant frequency.

24. The device of claim 23, wherein said device further includes a housing and wherein a first one of said resonant masses is enclosed in said housing and a second one of said resonant masses is exposed and wherein said step of exposing said resonator to said target fluid includes exposing said second mass and at least a portion of said torsional spring to said target fluid.

25. The device of claim 24, wherein said resonator is maintained in a state where said exposed mass and said enclosed mass are kept at temperatures that are separated by less than 5° C.

26. The device of claim 19, further including a temperature sensing device, and wherein temperature of said resonator is measured at least two separate points, and wherein said measurements are utilized in arriving at a corrosion measurement.

* * * * *